United States Patent
Brown et al.

[11] Patent Number: 6,093,199
[45] Date of Patent: Jul. 25, 2000

[54] INTRA-LUMINAL DEVICE FOR TREATMENT OF BODY CAVITIES AND LUMENS AND METHOD OF USE

[75] Inventors: Peter S. Brown, Palo Alto; Mary Bellack, Redwood City; Mona Patel, San Francisco, all of Calif.

[73] Assignee: Endovascular Technologies, Inc., Menlo Park, Calif.

[21] Appl. No.: 09/129,682

[22] Filed: Aug. 5, 1998

[51] Int. Cl.⁷ .................................................. A61M 29/00
[52] U.S. Cl. .......................................................... 606/200
[58] Field of Search .................................. 606/200, 191, 606/194, 195, 198; 623/1, 12; 128/898, 899

[56] References Cited

U.S. PATENT DOCUMENTS

| | | |
|---|---|---|
| 4,140,126 | 2/1979 | Choudhury . |
| 5,078,726 | 1/1992 | Kreamer . |
| 5,258,042 | 11/1993 | Mehta . |
| 5,282,824 | 2/1994 | Gianturco . |
| 5,306,294 | 4/1994 | Winston et al. . |
| 5,405,379 | 4/1995 | Lane . |
| 5,456,713 | 10/1995 | Chuter . |
| 5,527,355 | 6/1996 | Ahn . |
| 5,562,724 | 10/1996 | Vorwerk et al. . |
| 5,562,726 | 10/1996 | Chuter . |
| 5,571,170 | 11/1996 | Palmaz et al. . |
| 5,571,171 | 11/1996 | Barone et al. . |
| 5,578,071 | 11/1996 | Parodi . |
| 5,578,072 | 11/1996 | Barone et al. . |
| 5,609,628 | 3/1997 | Keranen . |
| 5,665,117 | 9/1997 | Rhodes . |
| 5,674,276 | 10/1997 | Andersen et al. . |
| 5,683,449 | 11/1997 | Marcade . |
| 5,683,452 | 11/1997 | Barone et al. . |
| 5,690,671 | 11/1997 | McGurk et al. ......................... 606/200 |
| 5,693,084 | 12/1997 | Chuter . |
| 5,693,087 | 12/1997 | Parodi . |
| 5,700,285 | 12/1997 | Myers et al. . |
| 5,700,287 | 12/1997 | Myers et al. . |
| 5,709,713 | 1/1998 | Evans et al. . |
| 5,713,917 | 2/1998 | Leonhardt et al. . |
| 5,713,948 | 2/1998 | Uflacker . |
| 5,800,454 | 9/1998 | Jacobsen et al. ....................... 606/191 |
| 5,941,888 | 8/1999 | Wallace et al. . |
| 5,951,599 | 9/1999 | McCrory . |

FOREIGN PATENT DOCUMENTS

| | | |
|---|---|---|
| 0 820 726 A2 | 1/1998 | European Pat. Off. . |
| 02-255157 | 10/1990 | Japan . |
| WO 97/48357 | 12/1997 | WIPO . |

*Primary Examiner*—Michael Buiz
*Assistant Examiner*—Vikki Trinh
*Attorney, Agent, or Firm*—Fulwider Patton Lee & Utecht, LLP

[57] ABSTRACT

An intra-luminal device comprises a flow retainer and/or modulator for maintaining an embolic mass within an aneurysm and, optionally, for diverting or modulating fluid flow, and an anchoring element for fixating the retainer within a lumen in a patient's body. The retainer is introduced into the body lumen and positioned with the retainer across the entrance to a body cavity or a body lumen with an embolic mass disposed within to prevent the embolic mass from migrating into the patient's vasculature. The retainer may also be a diverter or modulator used to divert or modulate the luminal fluid flow to the entrance to the body cavity or lumen. The anchoring element, which may be attached to the retainer, is deployed to permanently secure the retainer within the body lumen in the desired position.

42 Claims, 3 Drawing Sheets

INTRA-LUMINAL DEVICE FOR TREATMENT OF BODY CAVITIES AND LUMENS AND METHOD OF USE

BACKGROUND OF THE INVENTION

The present invention relates to intravascular methods and devices for treating hollow spaces within a person's body such as aneurysms, fistulas, and other body cavities and lumens, and is particularly well adapted for the treatment of intra-cerebral aneurysms of the cerebrovascular vessels.

The use of intravascular devices for the treatment of aneurysms has received an increasing amount of attention in the past few years as both the methods and devices available for intravascular procedures have become safer. One such method involves the insertion of a foreign body, such as an occlusion coil, within the aneurysm to precipitate the formation of a clot or thrombus within to partially or completely occlude the aneurysm and thus seal off the aneurysm. This method typically poses the risk of the coil or ensuing thrombus migrating from the aneurysm to the parent artery and causing a thrombo-embolic stroke. This method is also limited to the treatment of aneurysms with small necks opening into the artery in order to ensure that the coil will remain within the aneurysm. In another approach, a plug is inserted into the neck of a saccular aneurysm to block off blood flow into the aneurysm. If the plug is not sized correctly it may fall out of the aneurysm and into the patient's vasculature. In addition, placement of such a plug necessitates intimate contact with the aneurysm, which can cause rupture of the aneurysm and hemorrhaging. Finally, attempts have been made to treat both saccular and fusiform aneurysms by deploying grafts within the vasculature and anchoring them on either side of the aneurysm. These grafts typically extend along the entire length of a fusiform aneurysm, or lie across the mouth of a saccular aneurysm, thereby completely blocking off the flow of blood to the aneurysm and relieving the pressure thereon.

One such graft is described in U.S. Pat. No. 5,693,087 for a Method for Repairing an Abdominal Aortic Aneurysm, and consists of a tube adapted to be disposed within an abdominal aortic aneurysm and having a wire woven into one end of the graft that can be expanded to sealingly engage the vessel wall. The tube is preferably made of DACRON® and other polyester materials, TEFLON®, TEFLON® coated DACRON® and porous polyurethane. U.S. Pat. No. 5,527,355 for Apparatus and Method for Performing Aneurysm Repair discloses an aneurysm graft with an array of staples at either end having outward protruding barbs that lodge into the vessel wall. In addition, an exterior band is placed around the vessel at the positions where the barbs protrude into the vessel wall. The bands may have a VELCRO® strap or a clasp, or may be heat sealed. In yet another approach to the problem, U.S. Pat. No. 5,405,379 discloses a Self Expanding Vascular Endoprosthesis comprising a sheet of resiliently flexible biocompatible material such as polypropylene. The sheet is rolled upon itself about one of its longitudinal edges and is introduced adjacent to the aneurysm through a catheter to be expelled and expand to form a bridge isolating the aneurysm from the flow of blood.

Although potentially successful in such applications as abdominal aortic aneurysms, such devices do present a few drawbacks, especially in applications such as intracranial aneurysms. Among the more notable of the difficulties presented is the need to fit such devices through a very small delivery lumen along a typically very tortuous pathway. In addition, the longer the graft the larger the surface area for clot formation and endothelial cell growth, which in extreme situations can cause new complications for the patient. Also, these devices do not have the ability to be deployed, detached and/or retrieved as would be necessary for such a device in the intra-cranial vessels. The risks posed by these devices increase in magnitude when the end organ is the brain, with its smaller vessel diameters, weaker vessel walls, and increasingly tortuous paths. The devices described above are thus less than ideally suited to intracranial intravascular intervention.

Moreover, any device placed in the parent artery of an intracranial aneurysm runs the risk of occluding perforating side branches. These perforators are small, usually less than 200 microns in diameter, and can be the sole source of blood flow to important tissues of the brain. Presently known devices such as vascular grafts and stents can easily partially or completely block the flow of blood to one or more such perforators, thereby causing clinically significant ischemic strokes.

In light of the above, it becomes apparent that there continues to be a need for a method to treat an aneurysm to minimize the risk of rupture by relieving or minimizing the stress placed upon it by the arterial blood flow with a device that can be delivered easily to an intracranial site, deployed accurately, and used by itself or in conjunction with other methods and devices to augment their efficacy.

SUMMARY OF THE INVENTION

The present invention addresses the above mentioned needs by providing a method and device for treating a body cavity or lumen, such as a saccular aneurysm, by securing coils and other embolic devices deployed within the aneurysm or the aneurysm neck with devices that comprise a retainer element for placement across the entrance to the aneurysm and one or more anchoring elements for securing the device at the selected intravascular site. Such devices can be inserted through small diameter, tortuous vasculature with relative ease, deployed with accuracy, and secured at the target site with minimal adverse impact upon the surrounding tissue. A device according to the present invention also poses much reduced risk of blocking off flow to perforators and other small blood vessels, and thus is much safer to the patient when compared with other intra-luminal devices that are placed in the parent artery. In addition, the device is particularly well suited for treating saccular aneurysms originating near a vessel branch.

In the preferred method of use, the device of the present invention is used in conjunction with other aneurysm treatment methods to enhance the efficacy and safety of these methods. Thus, an embolic mass such as an occlusion coil is introduced into an aneurysm to induce clot formation, following or prior to which the device of the present invention is deployed with the retainer element across the aneurysm neck to ensure that neither the occluding element nor any clots migrate out of the aneurysm and out into the vasculature. This approach is particularly beneficial in wide necked aneurysms where embolic agents have until now been difficult or impossible to keep in. Alternatively, an embolic agent may be introduced into the aneurysm to substantially fill the aneurysmal cavity, following or prior to which the device of the present invention may be deployed with the retainer element across the entrance of the aneurysm to ensure that the embolic agent does not migrate into the vasculature of the patient. In another alternative method, the retainer element may incorporate medicine that is slowly released into the aneurysm following deployment of the device to enhance or prevent clot formation, cell growth, scar tissue formation, and other desirable or undesirable effects.

A further and important aspect of the device of the present invention is its ability to be detachably connected to the delivery device, which may be a guide wire, optic fiber, or catheter, so as to permit the operating surgeon to accurately deploy and, if necessary, redeploy the device with a high degree of accuracy. Once properly deployed both in terms of position and orientation with respect to the target cavity or lumen, the device may be detached from the delivery device and permanently deployed within the patient's vasculature.

The anchoring elements are preferably of the expandable type, such as coils or stents, so as to permit the device of the present invention to be inserted into the vasculature and to follow a relatively tortuous pathway to the desired intravascular location. In this manner the device of the present invention may be formed from a self-expanding shape memory alloy, or alternatively may be deployed using balloon catheters of the type known and used in the art. Thus, in one preferred embodiment, the device is comprised of self-expanding retainer and anchoring elements that can assume a linear or stretched configuration for insertion and delivery through a catheter or over a guide wire, and when the device is deployed in the artery, it has a memory that returns the elements to their coiled, expanded configuration and thus anchor itself to the patient's vasculature at the target intravascular site.

In another aspect, the device of the present invention can be used to treat a substantially hollow space or volume in a patient's body having fluid flowing within (such as, for example, a body cavity such as an aneurysm, or a body lumen such as a fistula or a vein) by reducing at least partially the peak fluid flow and peak fluid pressure experienced by the cavity or lumen. Therefore, in an alternative aspect the present invention provides a device comprising a diverter for diverting at least partially the arterial blood flow away from the entrance of a body cavity or lumen, and one or more anchoring elements attached to the diverter for securing the diverter at a particular intravascular location and, for certain embodiments, in a particular angular orientation with respect to the entrance of the cavity or lumen. For example, the diverter may operate to divert all or a portion of the arterial blood flow away from the neck of an aneurysm, or to completely block all such blood flow into the aneurysm, to the net effect of reducing the peak blood pressure experienced by the aneurysm. The diverter may be comprised of one or more coils, ribbons in parallel or intertwined configurations, flexible membranes, foam pads, and other elements formed with protrusions or surfaces for biasing the arterial blood flow in a particular direction.

In yet another aspect of the present invention, a device is provided including a modulator for altering the blood flow at a preselected intravascular location relative to the entrance of a body cavity or lumen so as to reduce the peak blood pressure experienced within. Such a device may be used to treat saccular or fusiform aneurysms. Depending upon the design of the modulator, the device may be deployed upstream or downstream of the entrance of the aneurysm. The device further includes one or more anchoring elements for securing the modulator at the intravascular location. The modulator may be comprised of any of the elements mentioned previously, as well as uni- or bi-directional valves.

DETAILED DESCRIPTION OF THE PREFERRED EMBODIMENTS

Figure 1A:
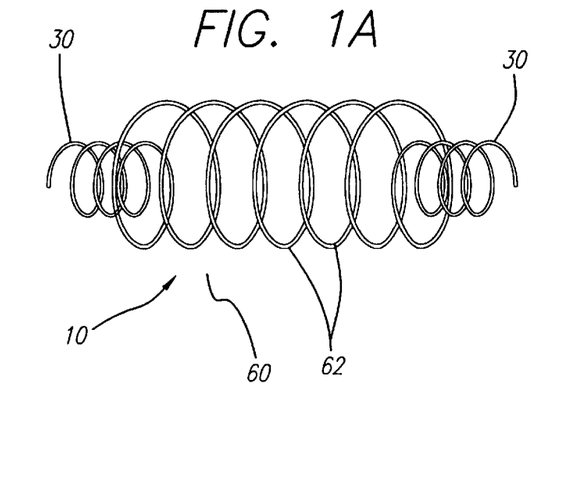
FIGS. 1A and 1B depict a frontal view and an end view of an intra-arterial device for the treatment of aneurysms according to the present invention.
Figure 1B:
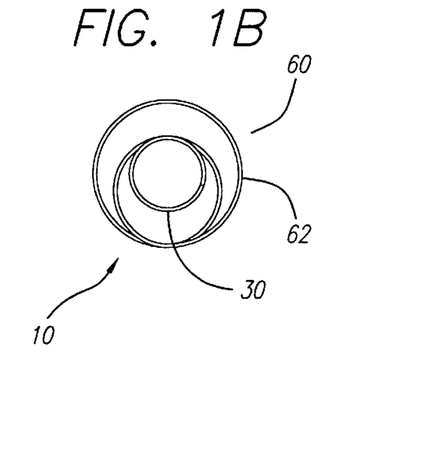

In the preferred embodiment, the present invention addresses the need for a method to treat a cavity or lumen connected to a patient's vasculature, by acting to retain and secure one or more embolic masses or elements disposed in the cavity or lumen for the purpose of occluding the cavity or lumen to the fluid flowing into it. With reference to FIGS. 1A and 1B, wherein a device for treating a saccular aneurysm is depicted, the present invention provides device 10, comprised of a retainer element in the form of a helical coil 60 and at least one anchoring element 30 attached to the retainer. The embodiment depicted in FIG. 1 comprises two anchoring elements 30, attached one each on either side of the retainer 60. The retainer coil may be of the same or larger radius than the anchoring elements, because the vessel region immediately adjacent to the entrance of an aneurysm will typically be enlarged in diameter, and the use of an enlarged coil retainer will also serve to further anchor the device in the proper position because the retainer coil will be able to better lodge itself against the vascular walls at this location.

In the preferred construction of device 10, the retainer and the anchoring elements are formed from a tightly coiled, small radius primary coil [not shown] that is wound into a secondary helical coil configuration having a larger radius approximately equal to the radius of the patient's vasculature at the target site. Such a construction offers improved flexibility and thus allows the device to better navigate tortuous pathways such as found in the intracranial vasculature, as well as increased resistance to compressive forces and thus enhanced 'pushability' and ability to be delivered through small diameter micro-catheters. In addition, a small radius primary coil construction provides increased strength when deployed into a secondary coil configuration as compared to a helical coil of the same diameter that is constructed from a straight wire, and can thus better anchor itself within the patient's vessel and resist the compressive forces exerted by the vessel wall. Furthermore, a primary coil also imparts to the device the ability to be delivered over a guidewire disposed within the interior of the primary coil.

As described elsewhere in the specification, the purpose of retainer 60 is to retain embolic devices or materials, such as micro coils or embolic liquids, deployed within the aneurysm and prevent the embolic devices from migrating out of the aneurysm and into the patient's vasculature. In addition, retainer 60 will also serve to block or divert at least a portion of the blood flow away from the entrance to the aneurysm, and for this reason the spacing between individual coils 62 of the retainer coil may also be adjusted to provide varying degrees of blood flow resistance. The coils may also have coatings applied to them, such as a layer of foam or rubber, that may help the coils of the retainer form a good seal therebetween. The coil may be circular or eccentric in cross section, depending upon the particular vascular geometry of each aneurysm deployment site. To fully utilize this advantage of the device of the present invention, as detailed elsewhere in the specification, it is crucial that the surgeon be able to precisely and accurately deliver and position the device prior to permanent deployment.

The embodiment depicted in FIG. 1 may also be formed with a retainer coil comprised of wire that has a cross section larger than the wire forming the anchoring elements. The wire comprising retainer 60 may additionally differ from that of anchoring elements 30 not only in terms of cross sectional area but also cross sectional geometry. Thus, the retainer portion of device 10 may be formed in a flattened configuration with a broad rectangular cross section forming a ribbon that assumes a ring shape when deployed at the aneurysm site. The ribbon forming the retainer may lie at different angular orientations relative to the wall of the artery, depending upon the impact on the arterial blood flow that is desired, and thus a ribbon sharply angled with respect to the arterial wall will produce greater turbulence in the arterial blood flow than a ribbon that is substantially parallel to the arterial wall.

With more particular reference to FIG. 1B, retainer 60 is disposed along the periphery of device 10 substantially in line with, or alternatively, radially outside of, the circumference of anchoring elements 30, so as to engage the vascular wall directly adjacent to the entrance to the aneurysm when the anchoring elements are deployed in the patient's vessel. As more fully described infra, in use device 10 is deployed with retainer 60 overlying the entrance of the target aneurysm so as to partially or fully block the flow of blood into the aneurysm and to retain an intra-saccular coil or other embolic device disposed within the aneurysm.

Anchoring elements 30 are comprised of helical coils and serve to secure the retainer over the entrance of the aneurysm by engaging the wall of the patient's blood vessel. The coils are preferably of a self-expanding design and thus are preferably fabricated of a material such as stainless steel or a shape memory alloy such as nickel titanium. Alternatively, the anchoring elements may be deployed through the application of radially outward expansive force, such as provided by a dilatation balloon as detailed infra. The use of an elastic, high hoop strength material such as stainless steel assures that the anchoring elements will continue to remain in secure contact with the vessel wall over extended periods of time.

In an alternative embodiment [not shown] of the device depicted in FIG. 1, device 10 may additionally be formed with a core wire connected to the free end of either anchoring element 30 and extending longitudinally through the interior of device 10 towards the free end of the other anchoring element disposed on the opposite side of retainer 60. Such a design offers the ability to use different materials in the construction of the device, thereby imparting various physical characteristics to the device. For instance, the core wire may be formed from shape memory alloys such as nickel titanium, thereby imparting superior shape memory retention characteristics to the device and causing it to better expand to a secondary, deployed configuration when delivered into the body through a device such as a catheter, while the retainer and/or anchoring elements may be formed from a radiopaque material such as platinum that will allow the operating surgeon to better visualize the position of the device within the patient's vasculature and thus assure accurate delivery and deployment. Conversely, the retainer and/or anchoring elements may be formed from a shape memory alloy, while the core wire is formed from a radiopaque material. Such a core wire construction may also be employed with a small radius primary coil wound into a secondary helical coil configuration, as detailed above, to further enhance the flexibility of such a coiled coil device.

Figure 2A:
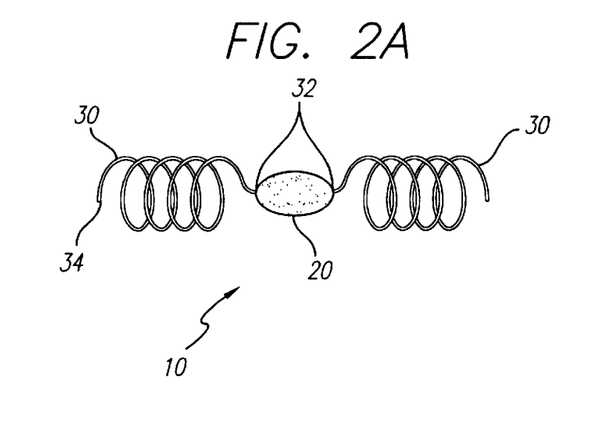
FIGS. 2A and 2B depict a frontal view and an end view of another embodiment of the intra-arterial device of the invention.
Figure 2B:
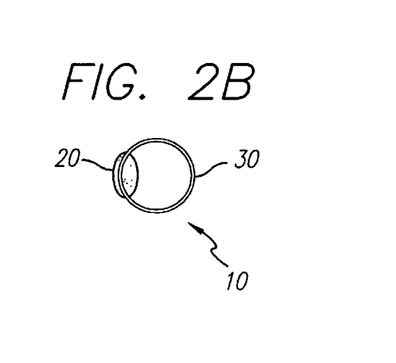

In another alternative embodiment, the device of the present invention addresses the need for a method to treat a substantially hollow space or volume in a patient's body having fluid flowing thereinto, such as a body cavity or a body lumen connected to the patient's vasculature, by relieving the stress placed upon it by the fluid (e.g. blood) flowing into it or by occluding the cavity or lumen to the fluid flow. The device is formed with a fluid flow modulator element for deployment in a particular, preselected intravascular location and orientation with respect to the entrance to the body cavity or lumen. With respect to the following alternative embodiments, like reference numbers are used for like elements. With particular reference to the embodiment shown in FIGS. 2A and 2B, device 10 comprises a fluid flow modulator in the form of a flow diverter element 20 and at least one anchoring element 30 attached to the diverter. The embodiment of the device of the present invention depicted in FIG. 2 comprises two anchoring elements 30, attached one each on either side of diverter 20. The diverter is comprised of a foam pad with an open cell, or alternatively closed cell, configuration. A closed cell diverter may be employed to block blood flow into the aneurysm, thereby maintaining the average pressure within the aneurysm at the level existent when device is initially deployed, and further also limiting the pressure pulses that the aneurysm will initially experience before the voids in the foam clot off. Alternatively, an open cell foam diverter will allow for a more compressible design that will facilitate intravascular delivery. Either type of foam will function equally well as a retainer for maintaining any embolizing devices or materials within the aneurysm. Moreover, foam diverters may also be doped with medicine and thus utilized as a drug delivery device. The diverter may also include a flexible membrane disposed across the foam pad to fully or partially cover the foam pad to enhance the ability of the device to isolate the aneurysm from the flow of blood. The diverter may be attached to the anchoring elements by any of a number of methods, such as gluing, melting, or welding. Alternatively, the two anchoring elements may be attached to one another by a longitudinal wire 32, such as would result if the two anchoring elements were formed from a single, continuous length of wire, and the diverter may be formed to wrap around the longitudinal wire. Materials suitable for forming the foam pad include polyurethanes, collagen, Poly-Sulphone™, hydrophilic plastics, silicone, and Cell Guard™.

Figure 3A:
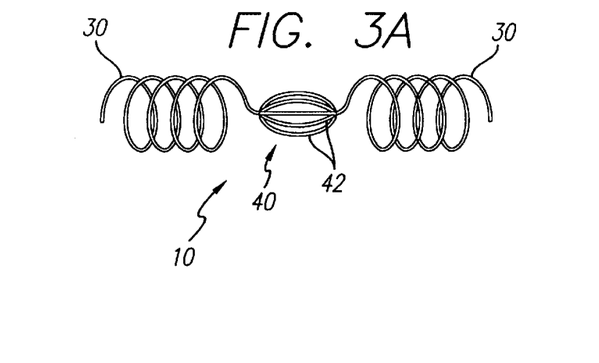
FIGS. 3A and 3B depict a frontal view and an end view of another embodiment of the intra-arterial device of the invention.
Figure 3B:
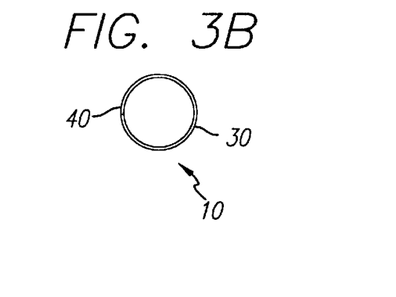
Figure 4A:
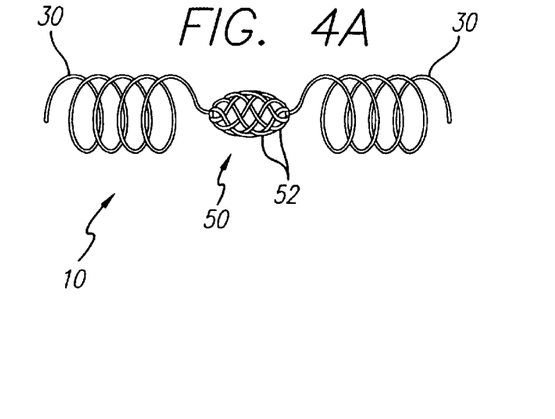
FIGS. 4A and 4B depict a frontal view and an end view of another embodiment of the intra-arterial device of the invention.
Figure 4B:
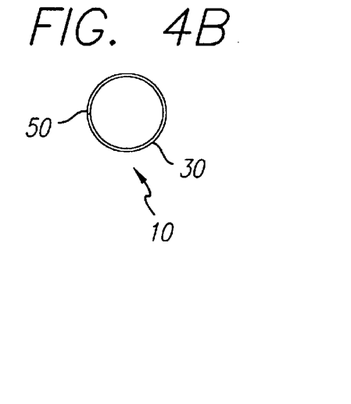

In the FIG. 3 embodiment of the invention, device 10 is similarly comprised of diverter 40 attached between a pair of anchoring elements 30. Diverter 40 is comprised of a plurality of ribbons 42 extending longitudinally between, and attached to, the anchoring elements. The ribbons may overlap or be spaced apart from one another to provide varying degrees of flow resistance to the blood flow of the patient. In addition, a flexible membrane may be disposed across the ribbons to partially or fully cover the diverter element. This diverter embodiment is likewise deployed directly across the entrance of the aneurysm. FIG. 4 depicts a variation of the embodiment of FIG. 3, whereby the ribbons 52 forming the diverter 50 are intertwined so as to form a mesh or filter. The diverter embodiments of FIGS. 3 and 4 can both be also employed as retainer elements, similar to the embodiment of FIG. 1.

Figure 5A:
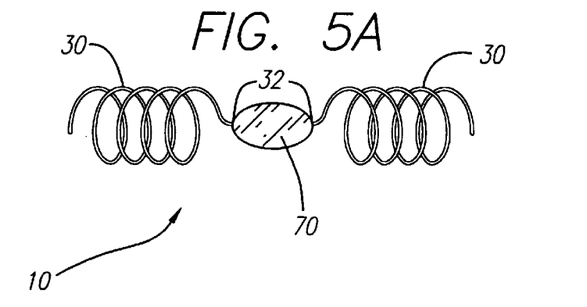
FIGS. 5A and 5B depict a frontal view and an end view of another embodiment of the intra-arterial device of the invention.
Figure 5B:
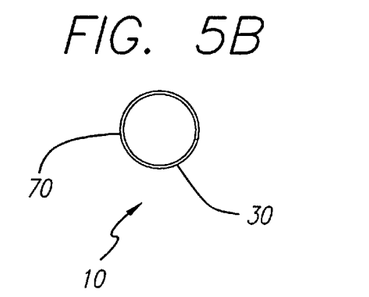

Referring to FIG. 5, the embodiment shown therein likewise comprises two anchoring elements 30 with diverter 70 attached therebetween. The diverter 70 is formed from an elastic membrane that is deployed over the entrance of the target aneurysm to block the flow of blood thereinto. The membrane may be attached to longitudinal wire 32 connecting the two anchoring elements, or alternatively may be mounted on a circumferential wire frame [not shown] that is in turn attached to the anchoring elements.

Figure 6A:
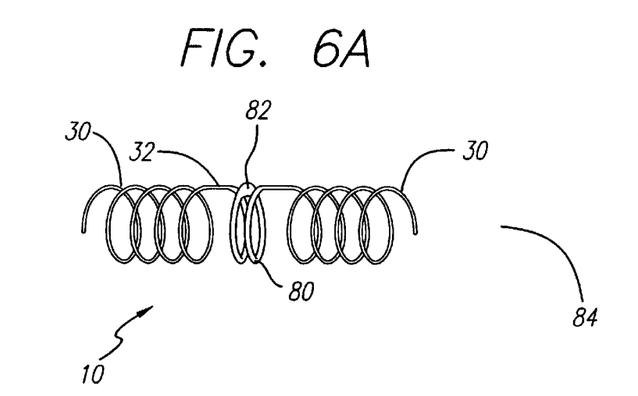
FIGS. 6A and 6B depict a frontal view and an end view of another embodiment of the intra-arterial device of the invention.
Figure 6B:
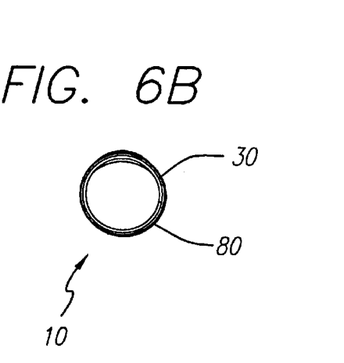

With reference now to FIG. 6, another embodiment of the present invention provides device 10 comprised of two anchoring elements 30 with a flow modulator element 80 disposed therebetween. The anchoring elements are interconnected by generally longitudinal wire 32, to which modulator 80 is attached by welding, brazing, gluing, or any other of a number of known methods. The function of the modulator is to alter the blood flow of the patient at a particular, preselected intravascular location adjacent to the entrance of the target aneurysm. This location may be upstream, adjacent to, or downstream of the entrance of the aneurysm, depending upon the configuration of the modulator.

Thus, for example, and with continued reference to FIG. 6, modulator 80 may be comprised of a ring element formed with an inner nub or protuberance 82 extending radially inward from its inner surface. Such device 10 is placed upstream of the entrance to the aneurysm and oriented with the nub disposed directly adjacent to the entrance. The nub operates to divert blood flow away from the entrance, thereby decreasing the amount of blood that enters the aneurysm and thereby the overall peak pressure experienced by the interior of the aneurysm. The ring element is formed as an open-ended coil that can be advanced through a catheter in a linear configuration and has shape memory properties that induce it to assume a circular configuration when unrestrained. In this manner the diverter may be advanced through a catheter to the deployment site. Alternatively, the diverter may be formed as a closed circular structure that is deployed by expandable devices such as balloons. The nub may take the form of an increased diameter portion along the coil, such as a secondary coil or a mass of material soldered or brazed onto the coil. Thus, as described previously, modulator 80 may take the form of a diverter element that diverts arterial blood flow away from the entrance to the aneurysm, or may be an element shaped to change the flow pattern around the entrance to the aneurysm without necessarily diverting the blood flow away from the aneurysm.

It must further be understood that the inventive concept of the present invention also encompasses the use of flow modulators to alter the fluid flow around the entrance to an aneurysm, fistula, or similar, substantially hollow cavity or lumen in a patient's body, and thus reduce the amount of fluid flowing into the entrance to the cavity or lumen, thereby reducing the overall peak pressure experienced by the tissue surrounding the cavity or lumen. Therefore, the treatment method of the present invention also encompasses the use of solely a modulator element, deployed intraluminaly within the patient's body to modulate or divert the flow of blood or other fluid from the entrance to the body volume to be treated. Thus, in an alternate embodiment of the device of the present invention, a flow modulator 80 as depicted in FIG. 6A may be formed with a multitude of coils and sized to fit within the vessel adjacent to an aneurysm so as to be capable of being securely deployed within the patient's vasculature without the use of a separate anchor element. Thus, any type of flow modulator element that is structurally adapted to being secured in a body lumen may be employed according to the method of the present invention to reduce the fluid pressure in a body space or volume. Due to the cylindrical nature of body lumens, such modulators will largely also be cylindrical in shape and formed with expandable geometries to engage the lumen walls for secure long term deployment. Thus, devices such as coils, stents, and balloons can all potentially be used to treat aneurysms by the method of the present invention.

Figure 7:
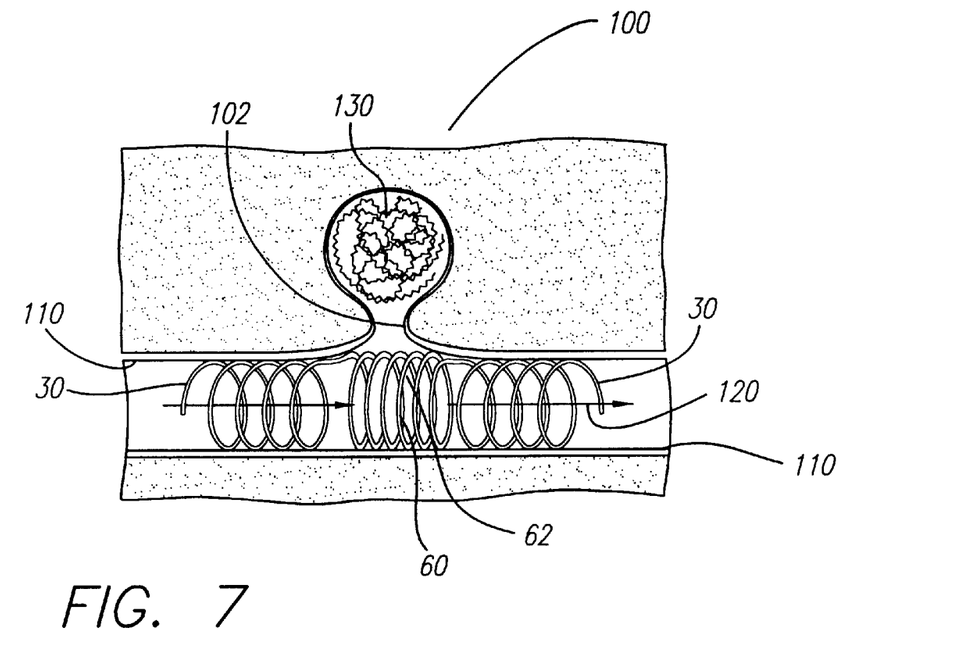
FIG. 7 is a frontal view, in partial cross-section, of the intra-arterial device of FIG. 1, deployed within the vasculature of a patient adjacent to the entrance of a saccular aneurysm having an embolic coil disposed within.

With reference to FIG. 7, in a preferred method of use of device 10 (using the embodiment of FIG. 1 discussed previously as an example), in a first step the device is formed from shape-memory alloys as discussed supra and is detachably connected to a delivery device such as a wire or optic fiber, examples of which are known in the art and are described, among others, in U.S. Pat. Nos. 5,605,162 and Re. 33,911. Methods suitable for attaching device 10 to the delivery device include mechanical, heat actuated, and electrolytical attachment methods, and are described, for example, in U.S. Pat. No. 4,735,201, U.S. Pat. No. 5,108,407, U.S. Pat. No. 5,122,136, U.S. Pat. No. 5,354,295, and U.S. Pat. No. 5,540,680. Thus, for example, the embodiment of FIG. 1 discussed previously, consisting of a retainer element disposed between two anchoring elements and having a core wire running longitudinally therethrough, may be attached to a guide wire through a portion of a material that is susceptible to electrolytic disintegration in blood when exposed to an electric current. Alternatively, the delivery device may comprise an optic fiber that is attached to the device of the present invention by a glue that melts when exposed to heat or light energy that is transmitted through the optic fiber.

In the next step, a catheter as described for example in U.S. Pat. No. 5,496,275, is inserted into the patient's vasculature and advanced to the site of target aneurysm 100 with the distal tip abutting the entrance to the aneurysm 102. An embolic device or material is then introduced through the catheter and into the interior of the aneurysm to fill the aneurysm and optionally induce clot and/or thrombus formation. The embolic device may be an embolic coil, wire, foam pad, neck plug, or any other structure that will substantially fill the aneurysm with its mass and/or any subsequently formed clots and/or thrombi. Such devices are described, for example, in U.S. Pat. No. 5,766,160, U.S. Pat. No. 5,766,219, and U.S. Pat. No. 4,994,069. Alternatively, an embolic material such as the compositions described in U.S. Pat. No. 5,580,568 and U.S. Pat. No. 5,667,767 may be introduced into the aneurysm through the catheter to solidify therein and thus occlude the aneurysm.

Device 10 can next be formed, or stretched, into a substantially linear configuration and inserted into the catheter to be delivered therethrough to the site of the aneurysm by the delivery device, which is advanced through the catheter from outside of the patient's body either manually by the surgeon or by an afterloader device. At the site of the aneurysm the device is advanced out of the distal tip of the catheter. Once deployed within the body, the device proceeds to assume its secondary, curved configuration. As previously described, the anchoring elements or alternatively the core wire is preferably formed from a radiopaque material, such as platinum or stainless steel, thereby allowing the surgeon to track the progress and position of the device within the vasculature of the patient by any known method or apparatus, including fluoroscopy, ultrasound, or magnetic imaging. If the device is not deployed properly either in terms of position or radial orientation with respect to the entrance to the aneurysm, it is retracted back into the catheter by pulling the delivery wire or fiber, where it once again assumes its linear configuration, and the catheter can then be repositioned or torqued into a different orientation by the surgeon from outside of the patient.

Once the surgeon determines that catheter placement is optimal, the device is redeployed out of the catheter, at which time the anchoring elements deploy against vessel wall 110 of the patient's vasculature to secure the device therein. The surgeon can now actuate the attachment mechanism connecting the device to the wire to detach the device from the wire and leave it permanently implanted in the patient's vasculature. Thus, as discussed previously, an electric current may be applied to the delivery wire to cause electrolytical corrosion of a portion at the distal end of the wire to which device 10 is attached, thereby releasing the device from the wire. Alternatively, the delivery device may be an optic fiber through which light energy is transmitted to a heat susceptible mass of glue that holds device 10 attached to the distal end of the optical fiber and that melts when exposed to the light or the heat generated by the light transmitted through the optic fiber. In the deployed position the retainer is biased snugly against the entrance to the target aneurysm, and the coils of the retainer act as a barrier to the embolic device or material within while also acting as a filter across the entrance, thereby reducing the amount of blood reaching the entrance and eventually the interior of the aneurysm, and thus also reducing the peak blood pressure inside the aneurysm.

Alternatively, the embolic device or material may be introduced into the aneurysm after device 10 has been deployed, thereby reducing the likelihood that the embolic mass will migrate from within the aneurysm before device has been deployed to secure it therein. In order to practice this method of use of the present invention, the retainer of device 10 must be formed in a configuration that allows the embolic device or material to be delivered therethrough. For instance, the coil retainer depicted in FIG. 1, the ribbon diverter of FIGS. 3 and 4, and the coil modulator of FIG. 6 can all be employed in this manner of use of the device of the present invention.

Figure 8:
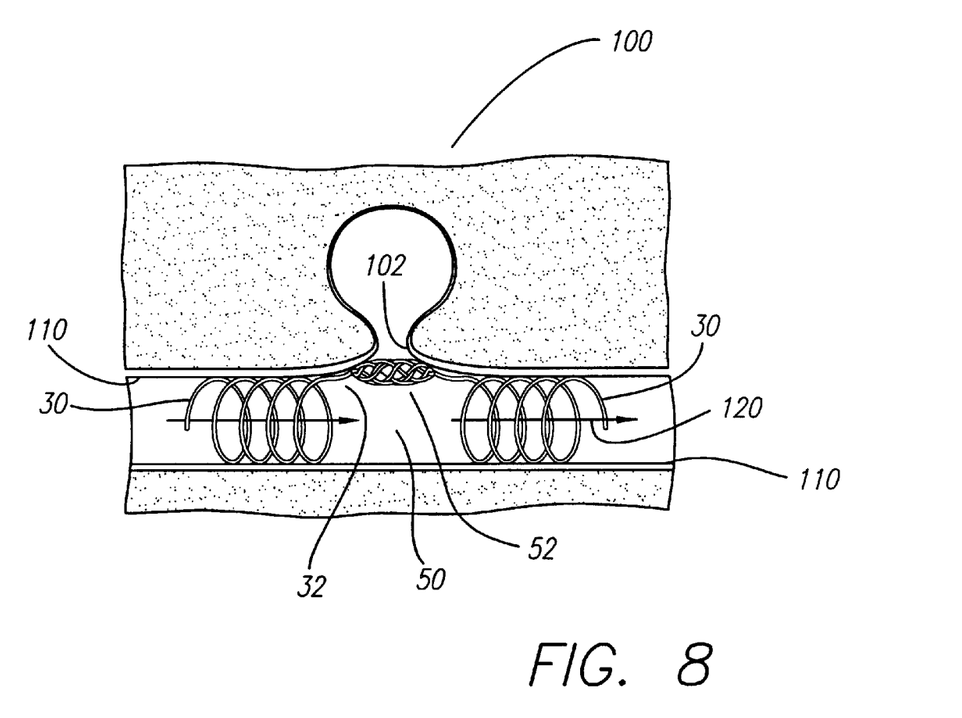
FIG. 8 is a frontal view, in partial cross-section, of the intra-arterial device of FIG. 4, deployed within the vasculature of a patient adjacent to the entrance of a saccular aneurysm.

With reference now to FIG. 8 [depicting use of the embodiment of FIG. 4], in another preferred method of use of the device of the present invention, the device is first mounted upon the balloon of a conventional balloon catheter of the type known in the art for delivering stents and the like, such as are described, for example, in U.S. Pat. No. 5,449,343 and U.S. Pat. No. 5,709,658, so that both anchoring elements overlie the balloon along the entire length of each anchoring element. The placement of the diverter along the periphery of the device facilitates this mounting procedure because it leaves the interior of the device relatively unobscured for the balloon to be inserted therein. Once the device has been securely mounted to the balloon of the delivery catheter, the physician may proceed to insert the catheter into the vasculature of the patient and advance the balloon with the device towards the site of the target aneurysm until the device is positioned such that the diverter is adjacent to the entrance of the aneurysm. Because the device is securely mounted to the balloon of the delivery catheter, the surgeon may repeatedly reposition the device by withdrawing and reinserting the catheter until the device is optimally positioned adjacent to the aneurysm. The device of FIG. 4, for example, must be positioned with the diverter overlying the entrance of the aneurysm, a task that the operating surgeon may easily accomplish by torquing the catheter so as to orient the diverter to cover the entrance of the aneurysm. Once the device has been properly positioned, the anchoring elements are deployed by dilating the balloon of the delivery catheter, thereby expanding the anchoring elements against the vessel wall of the patient and securing the device therein.

An important consideration in the use of the device of the present invention is the proper orientation of the retainer, diverter, or modulator element with respect to the entrance to the aneurysm. The ability to repeatedly insert and withdraw the device prior to permanent deployment is one method of allowing the surgeon to achieve the proper orientation. In addition, the device may be designed with a self-orienting feature, so as to automatically self-expand and deploy the diverter in the proper orientation with respect to the aneurysm. Such a self-orientation feature may, for example, be actuated by the flow of blood into the aneurysm, which creates a zone of lower pressure at the mouth of the aneurysm and which could thus help orient the diverter across the mouth of the aneurysm. Self-orientation could also be predicated upon the particular geometry of the deployment site, such as the enlargement of the native vessel diameter in close proximity to the mouth of the aneurysm, whereby the device may be sized and configured so as to fit in a specific orientation at the site.

In addition, the device of the present invention can also be used to promote scar tissue formation and endothelial cell growth by incorporating medicine into the retainer or modulator element for release over a period of time subsequent to deployment of the device. In such an application the retainer or modulator is preferably formed from a material exhibiting affinity for the particular medication to be applied, and may include polymeric material such as is described in U.S. Pat. No. 5,605,696. In this manner, the device of the present invention may be used to simultaneously practice two different methods for treating an aneurysm to reduce the likelihood of rupture, namely inducing cell growth to strengthen the aneurysm tissue and also reducing the peak blood pressure experienced by the aneurysm tissue.

The device of the present invention can also be employed to treat body lumens, such as arterial fistulas. A fistula is an alternate blood flow path that develops between an artery and a vein, and that may cause severe health problems by starving downstream tissue of blood as well as exposing other tissue to increased blood pressure. Typically coils have been used to embolize fistulas and thus block the alternate blood flow path. A device according to the present invention may instead be deployed with the retainer or modulator element placed across the arterial entrance to the fistula to block or divert the flow of blood away from the entrance to the fistula to reduce the amount of blood flowing into the fistula and thus alleviate the peak blood pressure experienced by the fistula and any surrounding tissue.

It must be understood that the embodiments detailed previously are for exemplary purposes only, and the present invention is not limited solely to these examples. Rather, the inventive concept comprised by the method and device of the present invention is the treatment of a body cavity or a body lumen through the intravascular placement of detachable fluid flow altering or blocking devices within the patient's vessel in the vicinity of the entrance of the cavity or lumen to prevent embolic devices and materials as well as the patient's blood from moving into and out of the cavity or lumen, thereby ensuring occlusion of the cavity or lumen and/or reducing the blood pressure adjacent to and at the entrance of the cavity or lumen. Thus, the present invention also allows the treatment of an aneurysm or a fistula without necessitating the placement of any foreign objects within the aneurysm itself or its entrance. In addition, once positioned, the device of the present invention is securely deployed within the patient's vessel and poses no risk of becoming dislodged and drifting downstream to potentially cause a stroke or other complications.

The anchoring elements described above are likewise not intended as limitations upon the practice of the present invention, but are rather merely illustrative. Thus, a retainer or modulator element may be deployed with a single anchoring element, or alternatively three or more anchoring elements, depending upon the topography of the particular intravascular deployment site. In addition, the anchoring elements may consist of any one of a number of expanding, stent or stent-like devices, and are not limited solely to helical coils. In addition, the anchoring elements may be of the self-expanding type, such as for example shape-memory devices formed from NiTi and other shape memory alloys, or of high modulus of elasticity stainless steel.

The anchoring elements are typically used to attach the device to the delivery vehicle, although the present invention also encompasses the concept of attaching the diverter or modulator element of the device to the delivery vehicle. Attachment may be mechanical, as for example mounting the anchoring elements upon the balloon of a catheter, or attaching the diverter or modulator or at least one of the anchoring elements to a wire (such as through a releasable clasp or a threaded connector); or alternatively chemical (e.g. a glue that dissolves when exposed to blood) or electrochemical (e.g. welding the device to the wire with a material that corrodes in blood when electrically charged). A wide variety of possibilities exist for detachably connecting the device of the present invention to any intravascular delivery device, all of which are encompassed by the concept of the present invention.

Moreover, the anchoring element or elements may be separate from the diverter, and in use the diverter is first deployed at the preselected intravascular location, following which the anchoring element is deployed so as to anchor the diverter securely in place. Thus, by way of example, modulator 80 of FIG. 6A may be deployed through a catheter and positioned across the entrance to an aneurysm, in the manner described previously, with nub 82 overlying the entrance to the aneurysm. Once modulator 80 is properly positioned, anchoring element 30 can be introduced through the same catheter and deployed axially through the modulator, so that as the anchoring element expands against the vessel wall the modulator is further expanded and anchored against the vessel wall along with it. Such a method of use of the device of the present invention may be advantageous in certain situations where the particular configuration of the aneurysm intravascular site renders it difficult to deploy a modulator and anchoring element or elements simultaneously, such as in particularly tortuous vessels where an anchoring element attached to the modulator would make precise positioning of the modulator unwieldy and imprecise.

In a previously disclosed embodiment, both the diverter and the anchoring element were disclosed as comprising helical coils. It must be understood that the present invention encompasses the concept of structurally identical retainer and anchor elements, such as helical coils, that only differ in their intended function. Thus, for example, both the anchor and the retainer or modulator elements may comprise identical helical coils, whereby the anchor coil secures the retainer or modulator coil across the entrance to the target aneurysm. In an alternative embodiment of such a device, the turns of the helical coils comprising the retainer or modulator and the anchor elements may turn in opposite directions.

It will therefore be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An intra-arterial device for treating an aneurysm having an embolic mass disposed therein, comprising:
   a retainer, said retainer operating to prevent the mass from exiting out of the aneurysm;
   at least one anchoring element attached to the retainer to secure the device adjacent to the aneurysm and maintain the retainer positioned across the entrance to the aneurysm, said anchoring element defined by non-overlapping structure; and
   a fluid flow modulator, said fluid flow modulator including a member that provides said fluid flow modulator with a profile that is asymmetric and discontinuous to said anchoring element, said fluid flow modulator operating to effect fluid flow outside of the aneurysm.

2. The device of claim 1, wherein the retainer comprises a helical coil.

3. The device of claim 2, wherein the helical coil is comprised of a small radius primary coil having a large radius secondary helical configuration.

4. The device of claim 1, wherein the retainer comprises at least one ribbon.

5. The device of claim 1, wherein the retainer comprises a plurality of ribbons intertwined in a mesh configuration.

6. The device of claim 1, wherein the device further comprises a core wire attached to the at least one anchoring element and extending longitudinally through the interior of the device.

7. The device of claim 1, further comprising a second anchoring element attached to the retainer and generally opposite from the first anchoring element to further secure the device at the preselected intra-luminal location and maintain the retainer positioned across the entrance to the aneurysm.

8. The device of claim 1, wherein the at least one anchoring element comprises a permanently expandable element.

9. The device of claim 8, wherein the expandable element is a coil.

10. The device of claim 9, wherein the retainer is a coil having a diameter substantially the same as the at least one anchoring element.

11. The device of claim 9, wherein the retainer is a coil having a larger diameter than the at least one anchoring element.

12. The device of claim 1, wherein the retainer is a coil having a first diameter and a second expanded diameter and is permanently expandable from the first diameter to the second diameter.

13. The device of claim 8, wherein the expandable element is a stent.

14. The device of claim 1, wherein the device is comprised of a shape memory alloy.

15. The device of claim 6, wherein the retainer and the at least one anchoring element are comprised of a shape memory alloy and the core wire is comprised of a radiopaque material.

16. The device of claim 6, wherein the retainer and the at least one anchoring element are comprised of a radiopaque material and the core wire is comprised of a shape memory alloy.

17. A method for treating an aneurysm connected through an entrance to the vasculature of a body, comprising the steps of:

provisioning an intra-luminal device having a retainer, at least one anchoring element defined by non-overlapping structure attached to the retainer and a fluid flow modulator;

providing an embolic mass;

disposing the embolic mass within the aneurysm;

disposing the device intravascularly with the retainer positioned across the entrance to the aneurysm;

securing the device within the body vasculature by deploying the non-overlapping structure of the at least one anchoring element against a wall of the body vasculature; and configuring the device so that the fluid flow modulator is positioned to affect flow outside of the aneurysm.

18. The method of claim 17, wherein the retainer comprises a helical coil.

19. The method of claim 18, wherein the helical coil is comprised of a small radius primary coil having a large radius secondary helical configuration.

20. The method of claim 17, wherein the retainer comprises at least one ribbon.

21. The method of claim 17, wherein the retainer comprises a plurality of ribbons intertwined in a mesh configuration.

22. The method of claim 17, wherein the device further comprises a core wire attached to the at least one anchoring element and extending longitudinally through the interior of the device.

23. The method of claim 17, further comprising a second anchoring element attached to the retainer and generally opposite from the first anchoring element to further secure the device at the preselected intra-luminal location and maintain the retainer positioned across the entrance to the aneurysm.

24. The method of claim 17, wherein the at least one anchoring element comprises a permanently expandable element.

25. The method of claim 24, wherein the expandable element is a coil.

26. The method of claim 25, wherein the retainer is a coil having a diameter substantially the same as the at least one anchoring element.

27. The method of claim 25, wherein the retainer is a coil having a larger diameter than the at least one anchoring element.

28. The method of claim 17, wherein the retainer is a coil having a first diameter and a second expanded diameter and is permanently expandable from the first diameter to the second diameter.

29. The method of claim 24, wherein the expandable element is a stent.

30. The method of claim 17, wherein the device is comprised of a shape memory alloy.

31. The method of claim 22, wherein the retainer and the at least one anchoring element are comprised of a shape memory alloy and the core wire is comprised of a radiopaque material.

32. The method of claim 22, wherein the retainer and the at least one anchoring element are comprised of a radiopaque material and the core wire is comprised of a shape memory alloy.

33. The method of claim 17, wherein the embolic mass comprises an embolic coil.

34. The method of claim 17, wherein the embolic mass comprises an embolizing liquid.

35. The method of claim 17, wherein the step of disposing the embolic mass within the aneurysm occurs prior to the step of disposing the device intravascularly.

36. The method of claim 17, wherein the step of disposing the embolic mass within the aneurysm occurs subsequent to the step of securing the device within the body vasculature.

37. The device of claim 3, wherein the device further comprises a core wire attached to the at least one anchoring element and extending longitudinally through the interior of the device.

38. The device of claim 37, wherein the core wire is formed from a shape memory material and the device is formed from a radiopaque material.

39. The device of claim 37, wherein the core wire is formed from a radiopaque material and the device is formed from a shape memory material.

40. The method of claim 19, wherein the device further comprises a core wire attached to the at least one anchoring element and extending longitudinally through the interior of the device.

41. The method of claim 40, wherein the core wire is formed from a shape memory material and the device is formed from a radiopaque material.

42. The method of claim 40, wherein the core wire is formed from a radiopaque material and the device is formed from a shape memory material.

* * * * *

UNITED STATES PATENT AND TRADEMARK OFFICE
CERTIFICATE OF CORRECTION

PATENT NO. : 6,093,199
DATED : Jul. 25, 2000
INVENTOR(S) : Peter S. Brown, Mary Bellack, Mona Patel

It is certified that error appears in the above-identified patent and that said Letters Patent is hereby corrected as shown below:

Title page, under "FOREIGN PATENT DOCUMENTS", change "WO 97/48357", to read --WO 97/48351--.

Signed and Sealed this

Twenty-fourth Day of April, 2001

Attest:

NICHOLAS P. GODICI

Attesting Officer

Acting Director of the United States Patent and Trademark Office